United States Patent
Aach et al.

(10) Patent No.: US 6,295,336 B1
(45) Date of Patent: Sep. 25, 2001

(54) X-RAY EXAMINATION APPARATUS WITH DOSE CONTROL

(75) Inventors: Til Aach; Dietmar W. Kunz, both of Aachen (DE)

(73) Assignee: U.S. Philips Corporation, New York, NY (US)

( * ) Notice: Subject to any disclaimer, the term of this patent is extended or adjusted under 35 U.S.C. 154(b) by 0 days.

(21) Appl. No.: 09/421,344

(22) Filed: Oct. 19, 1999

(30) Foreign Application Priority Data

Oct. 19, 1998 (EP) .................................................. 98203515

(51) Int. Cl.$^7$ ...................................................... H05G 1/34
(52) U.S. Cl. .......................................... 378/108; 378/98.7
(58) Field of Search .................................. 378/108, 98.7, 378/97, 98.3, 98.12, 111, 112

(56) References Cited

U.S. PATENT DOCUMENTS

| | | | | |
|---|---|---|---|---|
| 4,797,905 | * | 1/1989 | Ochmann | 378/108 |
| 4,955,043 | * | 9/1990 | Nekovar | 378/108 |
| 5,029,338 | * | 7/1991 | Aichinger et al. | 378/99 |
| 5,119,409 | | 6/1992 | Nields et al. | 378/106 |
| 5,509,044 | * | 4/1996 | Horbaschek | 378/97 |
| 5,513,239 | * | 4/1996 | Mulder | 378/98.7 |
| 5,608,775 | * | 3/1997 | Hasseler et al. | 378/98.8 |
| 5,675,624 | * | 10/1997 | Relihan et al. | 378/98.7 |
| 5,778,044 | * | 7/1998 | Bruijns | 378/92.8 |
| 5,825,841 | * | 10/1998 | Timmer | 378/4 |

FOREIGN PATENT DOCUMENTS

| | | | |
|---|---|---|---|
| 4328784 | 3/1995 | (DE) | A61B/6/00 |
| 0779770 | 6/1997 | (EP) | H05G/1/36 |

* cited by examiner

*Primary Examiner*—Robert H. Kim
*Assistant Examiner*—Irakli Kiknadze
(74) *Attorney, Agent, or Firm*—John F. Vodopia

(57) ABSTRACT

An x-ray examination apparatus comprises an x-ray source for generating an x-ray image and an image analysis system derives brightness variations from the x-ray image and derives a dose control signal dependent on said brightness variations in order to control the x-ray source. The image analysis system derives a distribution of said brightness variations and derives the dose control signal from the distribution of brightness variations. Preferably, the image analysis system is arranged to derive the brightness variations from the processed image and a histogram analysis is employed to derive the dose control signal.

10 Claims, 1 Drawing Sheet

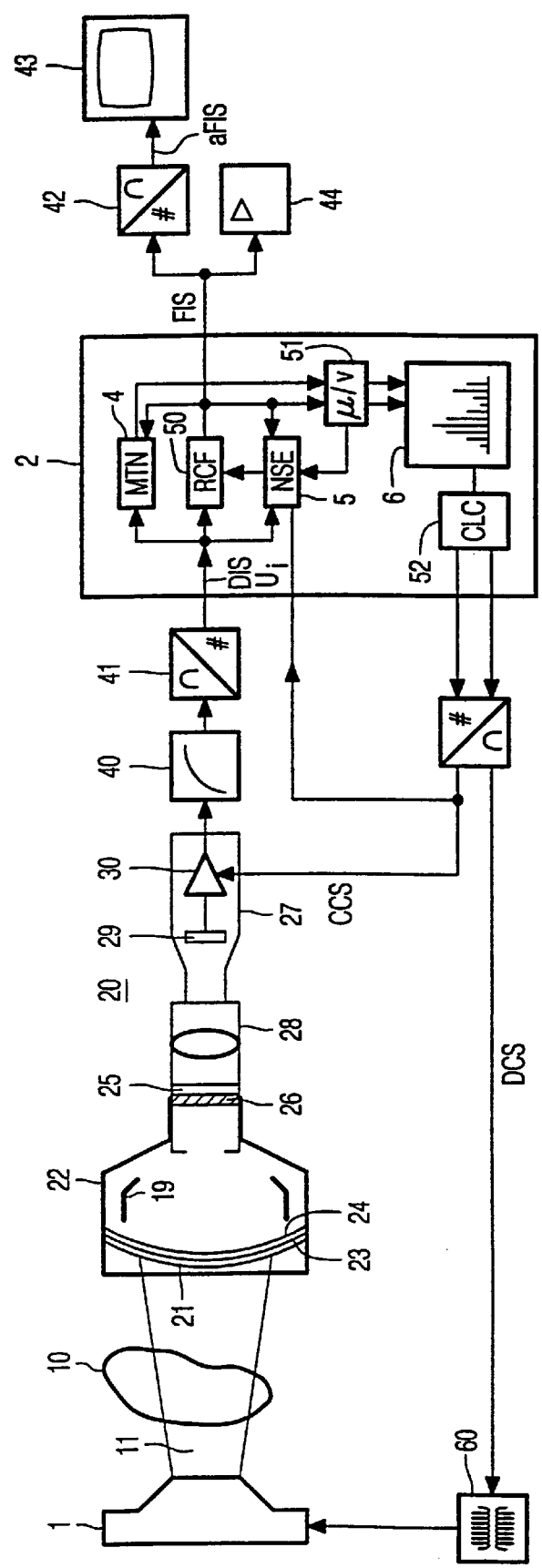

X-RAY EXAMINATION APPARATUS WITH DOSE CONTROL

BACKGROUND OF THE INVENTION

1. Field of the Invention

The invention relates to an x-ray examination apparatus comprising an x-ray source for generating an x-ray image and an image analysis system for deriving brightness variations from the x-ray image, and for deriving a dose control signal dependent on said brightness variations in order to control the x-ray source

2. Description of Related Art

Such an x-ray examination apparatus is known from German Offenlegungsschrift DE 43 28 784.

The image processor of the known x-ray examination apparatus is a temporal recursive filter which derives the processed image as a temporally filtered image from the x-ray image. The known x-ray examination apparatus comprises an image analysis system with a motion detection module for deriving brightness variations in the processed image which are due to motion in the processed image. In particular the motion detection module calculates these brightness variations as differences between brightness values at successive instants in time and in the same spatial position in the processed image. An amount of motion in the x-ray image is estimated from such differences between brightness values with the help of fuzzy logic rules. The motion in the processed image is motion in the temporally filtered image. The x-ray source of the known x-ray examination apparatus is adjusted on the basis of the amount of motion as estimated from the differences between brightness values. Notably, the x-ray source is adjusted to generate a high x-ray dose when the amount of motion is large and to generate a low-x-ray dose when the amount of motion is small.

The known x-ray examination apparatus employs a rather crude estimate of the amount of motion. As a consequence the x-ray source, in the known x-ray examination apparatus os adjusted rather inaccurately.

Citation of a reference herein, or throught this specification, is not to construed as an admission that such reference is prior art to the Applicants invention of the invention subsequently claimed.

An object of the invention is to provide an x-ray examination apparatus which can achieve more accurate adjustment of the x-ray source. A particular object of the invention is to provide an x-ray examination apparatus which can achieve accurate adjustment of the x-ray source which takes into account the amount of motion in the x-ray image more accurately for the adjustment of the x-ray source.

This object is achieved by an x-ray examination apparatus according to the invention which is characterized in that the image analysis system is arranged to derive a distribution of said brightness variations and derive the dose control signal from the distribution of brightness variations.

According to the invention, on the basis of the distribution of brightness variations it is determined to what extent the x-ray image is affected by noise and motion in the x-ray image. Local information, such as local brightness variations, is aggregated into a dose control signal that is an accurate and global i.e. a comprehensive representation of the amount of motion in the x-ray image. It has been found that brightness variations due to local image corruptions and brightness variations due to changes in significant areas of the x-ray image cause different distributions of brightness variations. The distribution of brightness variations notably allows corruptions of the x-ray image which do not substantially affect the diagnostic quality to be distinguished from image corruptions which deteriorate the diagnostic quality of the x-ray image. The diagnostic quality of the image is high when small details of little contrast are clearly visible in the image.

The dose control signal controls the x-ray source, in particular the dose control signal controls a high voltage supply for the x-ray source. On the basis of the dose control signal, the x-ray source is adjusted in such a manner that the x-ray dose is kept low when only insignificant image corruptions occur and the x-ray dose is set to a higher value when significant portions of the x-ray image are affected. The insignificant corruptions hardly affect the diagnostic quality of the x-ray image while significant corruptions seriously deteriorate the diagnostic quality. Notably when in the case of a low x-ray dose it appears that only insignificant image corruptions occur in the x-ray image, such isolated image corruptions are preferably reduced by filtering the x-ray image. Such isolated image corruptions, due to x-ray quantum noise, are preferably reduced by filtering rather than to avoid them by employing a higher x-ray dose. Insignificant image corruptions are, for example, caused by spurious isolated brightness variations or by small brightness variations. Significant image changes are caused, for example, by motion in the x-ray image, such motion may be due to a moving catheter, the beating of the patient's heart or the patient's respiratory motion. In areas where such a significant change occurs image corruptions due to, for example x-ray quantum noise cannot be removed by recursive filtering. This is because when if recursive filtering is applied to portions of the x-ray image containing a significant amount of motion, a series of after-images of the moving portion is generated. Such a series of after-images gives the impression of the moving portion having a tail of after-images.

The x-ray dose can be adjusted by adjusting the energy and/or the intensity of the x-rays emitted by the x-ray source.

These and other aspects of the invention will be elucidated with reference to the embodiments defined in the dependent Claims.

In a preferred embodiment of an x-ray examination apparatus according to the invention, the distribution of brightness variations is derived from a processed image rather than directly from the x-ray image itself. The image processing may involve recursive temporal filtering or spatial filtering of the brightness values of the x-ray image. In particular, the image processing involves adaptive recursive temporal filtering which is adjusted in dependence on an amount of motion in the x-ray image. The x-ray dose is controlled on the basis of the processed image, because the dose control signal is derived from a distribution of brightness variations in the processed image. Thus it is achieved that variations or changes in the image quality due to the processing are taken into account for the adjustment of the x-ray dose. Accurate adjustment of the x-ray dose is achieved; the x-ray dose is notably suitable for realizing a processed image with a high diagnostic quality, and a comparatively low x-ray dose is used. The processed image is displayed and used as a technical aid for making a diagnosis.

In a further preferred embodiment of the x-ray examination apparatus according to the invention, the brightness variations are derived from a comparison between previous brightness values of the processed image and present brightness values of the x-ray image. Differences between corresponding previous brightness values of the processed, i.e. filtered, image and present brightness values of the x-ray image notably represent mainly changes in the x-ray image due to motion when such differences are of large magnitude. Differences of small magnitude, however, are substantially due to small variations caused by x-ray quantum noise. Notably, motion in the image usually extends over a rather large number of pixels and hence results in brightness variations of about the same magnitude in many pixels, whereas isolated brightness variations are likely to be due to noise.

In a further preferred embodiment of an x-ray examination apparatus according to the invention, the distribution of brightness variations is formed on the basis of a motion quantity which is a function of the brightness variations. Thus the distribution is in fact formed from values of the motion quantity. The motion quantity is a decreasing function of the brightness variations. Preferably, the motion quantity has a gradual threshold in that for relatively large brightness variations the magnitude of the motion quantity is small. The magnitude of the motion quantity is large for small brightness variations. For either very small or very large brightness variations the motion quantity varies only very little as a function of the brightness variations; in an intermediate range between small and large brightness variations there is a transitional region in which the motion quantity gradually varies. The intermediate range of brightness variations gradually separates small brightness variations that are mainly due to x-ray quantum noise from large brightness variations that are mainly due to motion in the x-ray image. It has been found that the transitional region and other details of the motion quantity can be appropriately selected in an empirical way. The distribution of brightness variations on the basis of the motion quantity accurately represents the amount of motion relative to the amount of noise in the x-ray image. To this end, preferably the motion quantity is a function of the brightness variations due to motion relative to the brightness variations due to noise in the x-ray image. Notably the distribution of brightness variations on the basis of the motion quantity, i.e. the distribution of the values of the motion quantity, provides an accurate indication of the effect of image corruptions on the diagnostic quality of the x-ray image. On the basis of the distribution of the values of the motion quantity notably the presence of substantial image corruptions due to motion are distinguished from small or isolated corruptions that do not affect the diagnostic quality or can be reduced by filtering the x-ray image. Preferably, these brightness variations are derived from the processed image, notably an adaptively recursively temporally filtered image. The recursive filtering is advantageously controlled by the motion quantity so as to achieve stronger filtering the less motion there is in the x-ray image.

Because the motion quantity is a decreasing function of the brightness variations due to motion, it is avoided that large brightness variations are inadvertently discarded. Any large brightness variation due to motion gives rise to values of the motion quantity that are close to zero, so that such large brightness variations give rise to a substantial component of the distribution of the brightness variations due to motion at small values of the motion quantity. Hence, when the small values of the brightness variations are adequately taken into account, e.g. by considering all values of the brightness variations below some preselected ceiling value, even very large brightness variations due to motion can hardly be overlooked.

Preferably, the dose control signal is derived from a histogram of the values of the motion quantity. Such a histogram represents the distribution of the values of the motion quantity, i.e. the distribution based on the motion quantity of the brightness variations. The histogram of values of the motion quantity comprises the frequency of occurrence of values of the motion quantity. The histogram is formed by collecting the values of the motion quantity in predetermined intervals that are usually called 'bins'. The histogram represents the respective number of values of the motion quantity in the respective bins.

Preferably, a motion indicator value is derived from the histogram of the values of the motion quantity. The motion indicator value is accurately representative of the degree of substantial corruption of the x-ray image affecting the diagnostic quality of the x-ray image. In fact, the motion indicator value appears to be an accurate threshold value which separates irrelevant brightness variations from substantial image corruptions. In particular the motion indicator value is derived from one or more lower percentiles of the histogram of the values of the motion quantity. It appears that in practice the image corruptions which correspond to the lower 5%-percentile are spurious brightness variations that hardly affect the diagnostic quality of the x-ray image. On the other hand, brightness variations which correspond to the lower 10%-percentile already markedly deteriorate the overall diagnostic quality of the x-ray image. Thus, particularly accurate results are obtained when the motion indicator value is derived from the lower 5%- and 10% percentiles of the histogram of values of the motion quantity. The dose control signal is based on the motion indicator value so that the x-ray dose, i.e. the energy and/or intensity of the x-rays, is increased if there is a substantial amount of motion in the image and the x-ray dose is not increased when any image corruptions do not affect the diagnostic quality of the x-ray image or such image corruptions can effectively be reduced by filtering the x-ray image.

Preferably, the noise level in separate pixels in the processed image is computed from the actual x-ray dose, the noise level of previous brightness values of the processed image and the value of the motion quantity in the relevant pixel. The noise quantity is preferably a decreasing function of the noise level so that it is avoided that large brightness variations due to noise are inadvertently disregarded. The distribution of the noise quantity is formed from the values of the noise quantity in the separate pixels in the processed image. The calculation of the noise level in pixels in the processed image is based on the relation between the x-ray image and the processed image, notably as formed by the recursive temporal filtering that is controlled by the motion quantity. Because of the Poisson nature of the x-ray quantum noise, the noise level of the present brightness values of the x-ray image is accurately estimated from the actual x-ray dose, i.e. from the actual setting of the x-ray source. The distribution of the noise quantity reveals if brightness variations due to noise cause image corruptions that are insignificant or if the image corruptions cause significant deterioration of the diagnostic quality of the x-ray image.

Preferably, the noise level is represented by a noise indicator value that is derived from the histogram of brightness variations due to noise, notably from the lower 5% and lower 10% percentiles of the histogram of brightness variations due to noise. Notably the lower 5% percentile of the histogram appears to pertain to insignificant image corruptions and the lower 10% percentile of the histogram to image corruptions that are large enough to deteriorate the diagnostic quality. Hence, preferably a noise indicator value is derived from the lower percentiles of the histogram of the noise quantity. The noise indicator value forms an appropriate threshold that distinguishes insignificant image corruptions from deteriorations of the diagnostic quality.

Furthermore, the noise indictor values and the motion indicator values are derived as averages of the lower 5% and lower 10% percentiles of the histograms of the noise quantity and the histogram of the motion quantity, respectively. In this way stable results are obtained for the noise and motion indicator values such that sudden changes of the dose control signal derived from the noise and motion indicator values are avoided.

In a preferred embodiment of the x-ray examination apparatus according to the invention, the noise level of forthcoming brightness values of the x-ray image is derived from the present noise level of the processed image and the amount of motion as represented by the motion quantity, particularly by the motion indicator value. The noise level is accurately represented by the noise indicator value.

In practice the image is formed during a period of time. During said period of time noise and/or motion can occur in the image so that the signal level of the image signal varies in time. The brightness values of the image such as the x-ray image and of the processed image in practice are often represented by signal levels of an image signal. In particular, the image signal is an electronic video signal. The brightness variations are represented by differences between corresponding signal levels of the image signal at successive instants in time. Alternatively, the image at successive instants during said period of time can be regarded as a series of successive images and analogously the image signal at said instants as successive image signals. Brightness variations are then represented by differences of corresponding signal levels of successive image signals. Furthermore, signal levels of the image signal at successive instants or of successive image signals correspond when they relate to substantially the same position in the image.

BRIEF DESCRIPTION OF THE DRAWING

These and other aspects of the invention will be elucidated with reference to the embodiments described hereinafter and with reference to the accompanying drawing; therein:

The sole FIGURE is a schematic representation of an x-ray examination apparatus according to the invention.

DETAILED DESCRIPTION OF THE PREFERRED EMBODIMENTS

The FIGURE is a schematic representation of an x-ray examination apparatus according to the invention. The x-ray source irradiates a patient 10 who is radiologically examined with an x-ray beam 11. Because of local variations of the x-ray absorption in the patient 10, an x-ray image is formed on the entrance screen 21 of the x-ray detector 20. In the example shown in the FIGURE the x-ray detector is an x-ray image intensifier television chain. The entrance screen 21 of the x-ray image intensifier 22 comprises a conversion layer 23 and a photocathode 24. X-rays which are incident on the conversion layer generate low-energy radiation such as blue light or ultraviolet radiation whereto the photocathode is sensitive. The low-energy radiation causes the photocathode to emit electrons. The x-ray image intensifier also includes an exit window 25 on which a phosphorlayer 26 is provided. The electrons from the photocathode 24 are guided to the phosphor layer by an electron-optical system 19 which electron-optically images the photocathode on the exit window 25. The electrons from the photocathode 24 generate light or infrared radiation in the phosphor layer 25 so as to form an optical image on the exit window. The exit window 26 is optically coupled to the television camera 27 by means of an optical coupling 28. This optical coupling includes, for example a system of lenses or a fibre coupling. The television camera 27 includes an image sensor 29 which derives electrical charges from the light from the exit window 25. The image sensor includes a read-out register to derive an electrical image signal from the electrical charges; this image signal is fed to an adjustable amplifier 30. The adjustable amplifier 30 supplies an amplified image signal to a white-compression circuit 40. The white-compression circuit derives a compressed image signal from the amplified image signal. As the signal levels of the amplified image signal are higher, they are more compressed. Preferably, the white-compression circuit compresses the amplified image signal by taking the logarithm of the signal levels. The white-compression is calibrated or adjusted in such that a manner the dynamic range of the compressed image signal matches the input range of an analog-to-digital converter 41. The analog-to-digital converter 41 derives a digital image signal (DIS) from the compressed image signal and applies the digital image signal to the image analysis system 2. In an alternative embodiment, the x-ray detector is an x-ray matrix sensor which derives a digital signal from the x-ray image. In that embodiment a digital gain adjustment device and a digital white-compression unit are employed to form the digital image signal which is applied to the image analysis system.

The image analysis system 2 incorporates an image processing unit. The image processing unit is a recursive temporal filter 50 which reduces noise in the digital image signal. The recursive temporal filter 50 filters the digital image signal in which the noise level is reduced while the image information of the digital image signal is suitably maintained. The filtered image signal (FIS) is supplied to a buffer unit 44 for storing the filtered image signal for further processing or for printing on a hard-copy. The filtered image signal (FIS) is also applied to a digital-to analog converter 42 which derives an analog filtered signal (aFIS) which is applied to a monitor 43. The image information of the x-ray image is displayed on the monitor.

The image analysis system 2 incorporates the motion detection unit 4 and the noise detection unit 5 which derive the amount of motion and noise respectively in the digital image signal (DIS). The motion detection unit 4 and the noise detection unit 5 control the temporal recursive filter; specifically, the temporal recursive filter is controlled by the motion detection unit and the noise detection unit 5 via a functional unit 51 as will elaborated in the sequel. Furthermore, the image analysis system 2 derives the dose control signal which is employed to control a high-voltage generator 60 for the x-ray source 1.

The digital image signal DIS is applied to the temporal recursive filter 50. The signal amplitudes $U_i$ of the current digital image signal DIS are combined with the signal amplitudes of the digital image signal of a previous image or, in other words, of the image at a previous instant in time, $Y_{i-1}$, according to $$Y_i(x) = Y_{i-1}(x) + K_i(x)[U_i(x) - Y_{i-1}(x)], \qquad (1)$$

where x denotes the position in the image and $K_i$ is a filtering coefficient. The indices i−1 and i denote the successive instants. The motion detection unit 4 derives the amount of motion in the image from the signal levels of the digital image signal at successive instants. The motion detection unit computes the difference $d_i(x)=U_i(x)-Y_{i-1}(x)$. The digital image signal is also applied to the noise detection unit. In particular, the noise detection unit 5 is arranged to compute statistical variances or standard deviations. The noise detection unit 5 notably, computes the variances of the signal levels of the digital image signal and the filtered digital image signal, i.e. the noise detection unit 5 computes $$u_i^2(x) \equiv \text{Var} U_i(x),$$
$$\sigma_i^2(x) \equiv \text{Var} Y_i(x) \qquad (2)$$

and the variance of the difference $S_i^2(X)=\text{Var} d_i(x)=\sigma_{i-1}^2(x)+u_i^2(x)$. The variance $u_i^2(x)$ is computed by the noise detection unit from the x-ray intensity at the respective positions in the x-ray image while making use of the transfer characteristics of the image-intensifier television chain and the setting of the white-compression circuit. The variance of the previous filtered digital image signal $\sigma_{i-1}(x)$ represents the noise level of the previous filtered image. This variance $\sigma_{i-1}(x)$ has been calculated by the functional unit in the preceding iteration according to the formula (3) below. It is apparent that $u_i^2(x)$ is inversely proportional to the x-ray dose used to form the x-ray image. Hence, it is useful to write $$u_i^2(x) = \frac{g[U_i(x)]}{D_i},$$

where the function g represents the intensity dependency of the noise due to the Poisson nature of the x-ray quantum noise and the function g also represents the modulation transfer of the x-ray image intensifier television chain as well as the white compression. Furthermore, for the calculation of the variance of the difference statistical independence of the noise in successive images is assumed.

A functional unit 51 calculates the motion quantity from the difference and its variance, i.e.

$$\alpha_i(x) = \mu\left(\frac{d_i^2(x)}{s_i^2(x)}\right),$$

where $\mu$ is a smoothly decreasing function. In particular the function $\mu$ has a gradual threshold. This means that for high values, i.e. above some pre-set upper boundary of its argument, the function has a preset maximum value, for low values, that is below some pre-set lower boundary of its argument the function $\mu$ has a pre-set minimum value. Between the lower boundary and the upper boundary the function $\mu$ gradually increases from the minimum value to the maximum value. Preferably, the functional unit 51 comprises a look-up table in which the function $\mu$ is stored in the form of a table which assigns values of $\alpha_i(x)$ to input values of $d_i(x)$ and $s_i(x)$. Furthermore, the functional unit 51 calculates the filter coefficient:

$$K_i(x) = 1 - \frac{\alpha(x)u_i^2(x)}{\sigma_{i-1}^2(x)+u_i^2(x)}, \qquad (3)$$

The (local) filter coefficients $K_i(x)$ are employed to control the temporal recursive filter. In particular, less temporal recursive filtering is performed as the differences between signal levels, that is brightness values, at successive instants is larger. In other words, the image at the previous instant is taken less into account for the computation of the filtered image signal as the difference between the image at successive instants is larger. Furthermore, it is to be noted that the variance of the current filtered image signal is recursively determined from (1) and (2)

$$\sigma_i^2(x) = \frac{[1-\alpha_i(x)]u_i^2(x)+\sigma_{i-1}^2(x)}{\sigma_{i-1}^2(x)+u_i^2(x)}u_i^2(x) \qquad (4)$$

Thus, the noise level of the current filtered image is estimated form the current digital image signal and the previous filtered image signal. The computation of the variance of the current filtered image according to the relation (4) is carried out by the functional unit 51. The functional unit 51 also calculates a noise quantity $v_i^2(x)$ which is a decreasing function of the variance $\sigma_i^2(x)$. Particularly accurate results for the dose control signal have been achieved by using the ratio $$v_i^2(x) = \frac{g[Y_i(x)]}{\sigma_i^2(x)}.$$

The functional unit 51 applies the calculated noise and motion quantities and α and v to a counting unit which acts as both the motion-counting unit and the noise-counting unit. The counting unit 6 derives histograms of the noise quantity and the motion quantity. The counting unit derives noise and motion indicator values, $\hat{v}_i^2$ and $\hat{\alpha}_i$, respectively. The noise and motion indicator values typically represent an area of the x-ray image which on the one hand is large enough to be diagnostically relevant and on the other hand is of least quality with respect to noise and motion in the x-ray image. Preferably, the noise and motion indicator values are calculated as an average of the area in the respective histograms between the lower 5% and lower 10% percentiles. Furthermore, the image analysis system 2 is provided with a calculator 52 which is coupled to the counting unit 6. The calculator derives the dose control signal DCS from the lower 5% and lower 10% percentiles of the histograms. The dose control signal is applied to the high-voltage generator 60 of the x-ray source. Furthermore, the calculator 52 derives a camera control signal CCS which is applied to a control input of the adjustable amplifier 30 so as to control the gain of the adjustable amplifier.

The dose control signal DCS and the camera control signal CCS are set such that the camera gain is inversely proportional to the forthcoming dose. Furthermore, as the motion indicator value does not change much from one instant of the x-ray image to the next instant (i.e. is, $\alpha_{i+1} \approx \alpha_i$), it follows from (4) that the forthcoming dose is related to the local forthcoming value of the noise quantity as:

$$v_{i+1}^2(x) = \frac{v_i^2(x)+D_{i+1}}{[1-\alpha_i(x)]v_i^2(x)+D_{i+1}}D_{i+1} \qquad (5)$$

The dose control signal DCS is preferably set such that in substantially the entire x-ray image, i.e. possibly apart from negligible isolated portions, a predetermined noise level is not exceeded, provided that the (estimated) motion occurring in the x-ray image at the forthcoming instant is similar, as compared to the present image, to the motion that occurred between the present x-ray image and the previous x-ray image. Thus, for $v_i^2(x)=\hat{v}_i^2$ and $\alpha_i(x)=\hat{\alpha}_i$, the forthcoming dose $D_{i+1}$ is set such that $v^2_{i+1}(x)=T$, where T denotes an adjustable threshold that represents the acceptable noise level for the subsequent instant. Thus, in this manner the local information as represented by the local values of the noise and motion quantities are aggregated into a relation between the forthcoming dose value and the noise threshold T:

$$T = \frac{\hat{v}_i^2 + D_{i+1}}{(1-\hat{a}_i)\hat{v}_i^2 + D_{i+1}} D_{i+1} \quad (6)$$

This relation is in fact a quadratic equation for the forthcoming dose $D_{i+1}$, parameterized by the threshold value T. The forthcoming dose is easily derived from equation (6):

$$D_{i+1} = \frac{1}{2}\left[(T-\hat{v}_i^2) + \sqrt{(T-\hat{v}_i^2) + 4(1-\hat{a}_i)^2 T\hat{v}_i^2}\right]. \quad (7)$$

Hence, by setting a desired value for the forthcoming noise indictor value, the corresponding forthcoming dose value is calculated by the calculator 52 by computing the forthcoming dose value $D_{i+1}$ from the equation (7).

All references cited herein are incorporated herein by reference in their entirety and for all purposes to the same extent as if each individual publication or patent or indicated to be incorporated by reference in its entirety for all purposes.

What is claimed is:

1. An x-ray examination apparatus comprising:
an x-ray source for generating an x-ray image, and an image analysis system for processing the x-ray image including deriving brightness variations from the x-ray image, and for deriving a dose control signal dependent on said brightness variations in order to control the x-ray source, wherein the image analysis system processes the x-ray image to derive a distribution of said brightness variations and to derive the dose control signal from the distribution of brightness variations in order to control the x-ray source.

2. An x-ray examination apparatus as claimed in claim 1 further comprising an image processor for deriving a processed image from the x-ray image, and wherein the image analysis system is arranged to derive the brightness variations from the processed image.

3. An x-ray examination apparatus as claimed in claim 2 wherein the image analysis system is arranged to derive the brightness variations from previous processed brightness values of the processed image and present brightness values of the x-ray image.

4. An x-ray examination apparatus as claimed in claim 1 wherein the image analysis system further comprises an arithmetic unit for computing a motion quantity as a decreasing function of the brightness variations, and a motion-counting unit for deriving the distribution of brightness variations from said motion quantity.

5. An x-ray examination apparatus as claimed in claim 4 wherein the motion-counting unit is arranged to derive a histogram of values of the motion quantity, wherein the image analysis unit further comprises a motion-calculator to derive a motion-indicator value from the histogram of values of the motion quantity, and wherein the image analysis system is arranged to derive the dose control signal from the motion-indicator value.

6. An x-ray examination apparatus as claimed in claim 4 wherein the arithmetic unit is arranged to compute a noise level of brightness values of the processed image from a noise level of previous brightness values of the processed image, the actual setting of the x-ray source and the motion quantity, and to compute a noise quantity as a decreasing function of the noise level of brightness values of the processed image, and wherein the image analysis system further comprises a noise counting unit for deriving the distribution of brightness variations from said noise quantity.

7. An x-ray examination apparatus as claimed in claim 6 wherein the noise counting unit is arranged to derive a histogram of values of the noise quantity, and wherein the image analysis unit further comprises a noise-calculator for computing a noise-indicator value from the histogram of values of the noise quantity, and wherein the image analysis unit is arranged to derive the dose control signal from the noise-indicator value.

8. An x-ray examination apparatus as claimed in claim 5 wherein the motion-calculator is arranged to derive the motion-indicator value from one or more lower percentiles of the histogram of values of the motion quantity.

9. An x-ray examination apparatus as claimed in claim 7 wherein the noise calculator is arranged to derive the noise-indicator value from one or more lower percentiles of the histogram of the noise quantity.

10. An x-ray examination apparatus as claimed in claim 9 wherein the image analysis unit further comprises a noise estimator for deriving the noise level of forthcoming brightness levels of the processed image from the noise indicator value and the motion indicator value, and for deriving a forthcoming dose value from the noise level of the forthcoming brightness levels of the processed image, and wherein the image analysis unit is arranged to derive the dose control signal from the forthcoming dose value.

* * * * *